US00PP30373P3

(12) United States Plant Patent
van Langen

(10) Patent No.: US PP30,373 P3
(45) Date of Patent: Apr. 9, 2019

(54) ***ECHEVERIA* PLANT NAMED 'TSAECH1709'**

(50) Latin Name: *Echeveria hybrid*
Varietal Denomination: TSAECH1709

(71) Applicant: Tosjami B.V., Heerhugowaard (NL)

(72) Inventor: Gerard van Langen, Heerhugowaard (NL)

(73) Assignee: Tosjami B.V., Heerhugowaard (NL)

( * ) Notice: Subject to any disclaimer, the term of this patent is extended or adjusted under 35 U.S.C. 154(b) by 0 days.

(21) Appl. No.: 15/932,624

(22) Filed: Mar. 27, 2018

(65) Prior Publication Data

US 2019/0053414 P1 Feb. 14, 2019

(30) Foreign Application Priority Data

Aug. 9, 2017 (QZ) ..... PBR 2017/1945

(51) Int. Cl.
*A01H 5/12* (2018.01)
*A01H 6/00* (2018.01)

(52) U.S. Cl.
USPC ..... Plt./373
CPC ..... *A01H 6/00* (2018.05); *A01H 5/12* (2013.01)

(58) Field of Classification Search
USPC ..... Plt./373
See application file for complete search history.

*Primary Examiner* — Susan McCormick Ewoldt
*Assistant Examiner* — Karen M Redden
(74) *Attorney, Agent, or Firm* — Samuel R. McCoy, Jr.

(57) ABSTRACT

A new and distinct *Echeveria* hybrid plant named 'TSAECH1709' which is characterized by succulent foliage arranged in a compact basal rosette, light greyed-green glaucous foliage that is margined and tipped with pink, as well as the stability of these characteristics from generation to generation.

4 Drawing Sheets

Latin name of the genus and species: The Latin name of the genus and species of the novel variety disclosed herein is *Echeveria* hybrid.

Variety denomination: The inventive variety of *Echeveria* hybrid disclosed herein has been given the variety denomination 'TSAECH1709'.

CROSS REFERENCE TO RELATED APPLICATIONS

This application claims priority to the Community Plant Variety Rights application number 2017/1945, filed Aug. 9, 2017, which is herein incorporated by reference.

BACKGROUND OF THE INVENTION

Parentage: 'TSAECH1709' is a hybrid seedling selection resulting from the controlled pollination of an unnamed *Echeveria pulidonis* x *Echeveria* hybrid 'Perle von Nurnberg' hybrid plant (not patented), the seed parent, with an unnamed *Echeveria lilacina* plant (not patented), the pollen parent. The crossing was made by the inventor in the summer of 2013 at a commercial greenhouse in Heerhugowaard, the Netherlands. In the summer of 2014, one seedling was observed which exhibited unique growth and foliage characteristics. The seedling was isolated for further evaluation in order to confirm the distinctness and stability of the characteristics first observed. Upon confirmation of distinctness and stability, 'TSAECH1709' was selected for commercialization.

Asexual Reproduction: Asexual reproduction of the new cultivar 'TSAECH1709', by way of rooting leaf cuttings, was first initiated in the summer of 2015 at the inventor's commercial greenhouse in Heerhugowaard, the Netherlands.

Through three subsequent generations, the unique features of this cultivar have proven to be stable and true to type.

SUMMARY OF THE INVENTION

The cultivar 'TSAECH1709' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'TSAECH1709'. These characteristics in combination distinguish 'TSAECH1709' as a new and distinct *Echeveria* hybrid cultivar:

1. 'TSAECH1709' exhibits succulent foliage arranged in a compact basal rosette; and
2. 'TSAECH1709' exhibits moderately glaucous foliage; and
3. 'TSAECH1709' exhibits light greyed-green foliage that is margined and tipped with pink.

BOTANICAL DESCRIPTION OF THE PLANT

Figure 1:
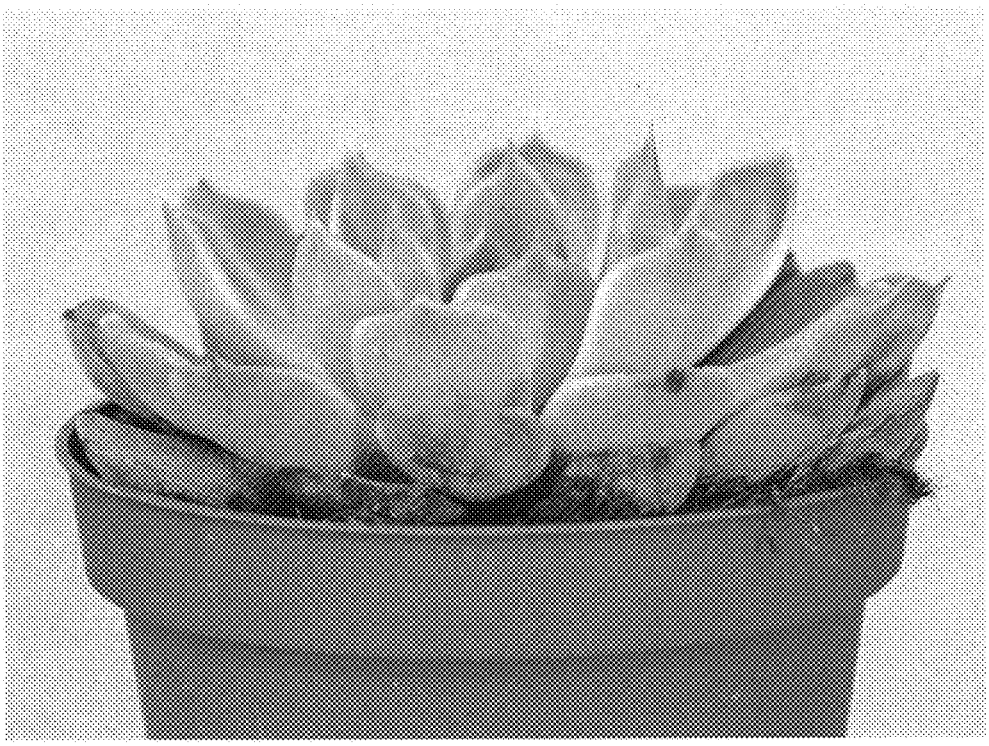
FIG. 1 illustrates, as nearly true as it is reasonably possible to make the same in color photographs of this type, an exemplary plant of 'TSAECH1709' grown in a commercial greenhouse in Heerhugowaard, the Netherlands. This plant is approximately 6 months old, shown planted in a 10 cm container.
Figure 2:
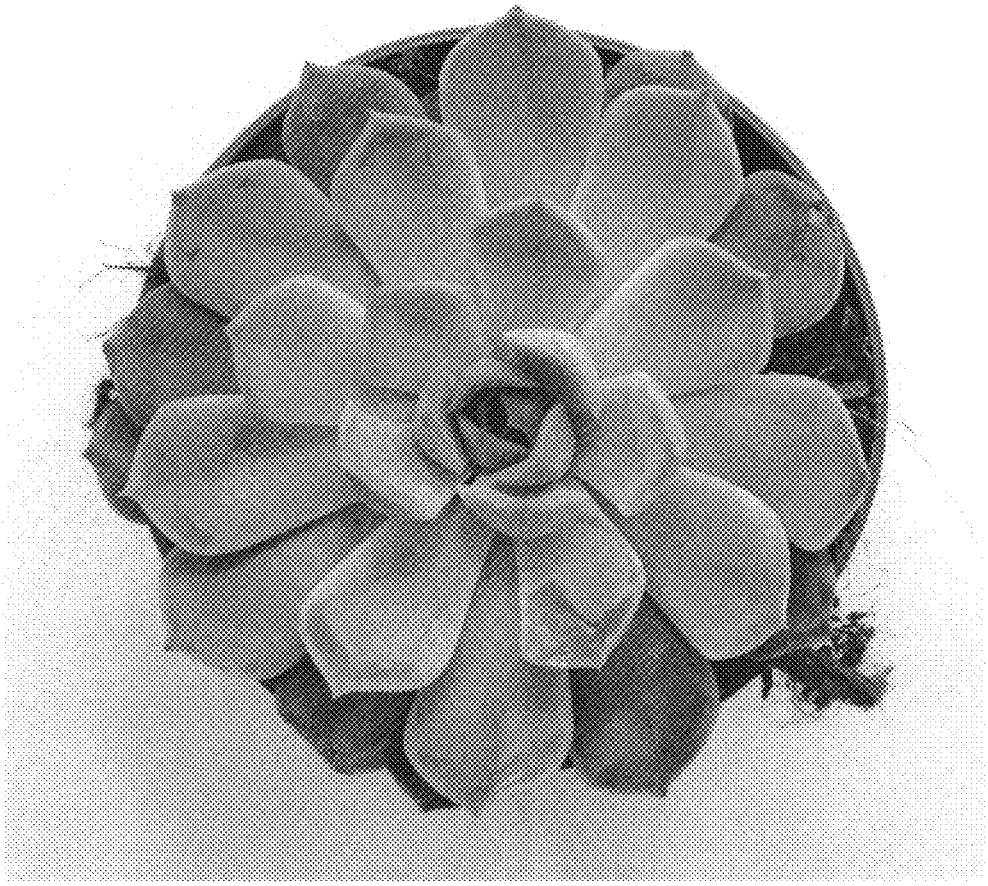
FIG. 2 illustrates, as nearly true as it is reasonably possible to make the same in color photographs of this type, the typical foliage arrangement of 'TSAECH1709'.
Figure 3:
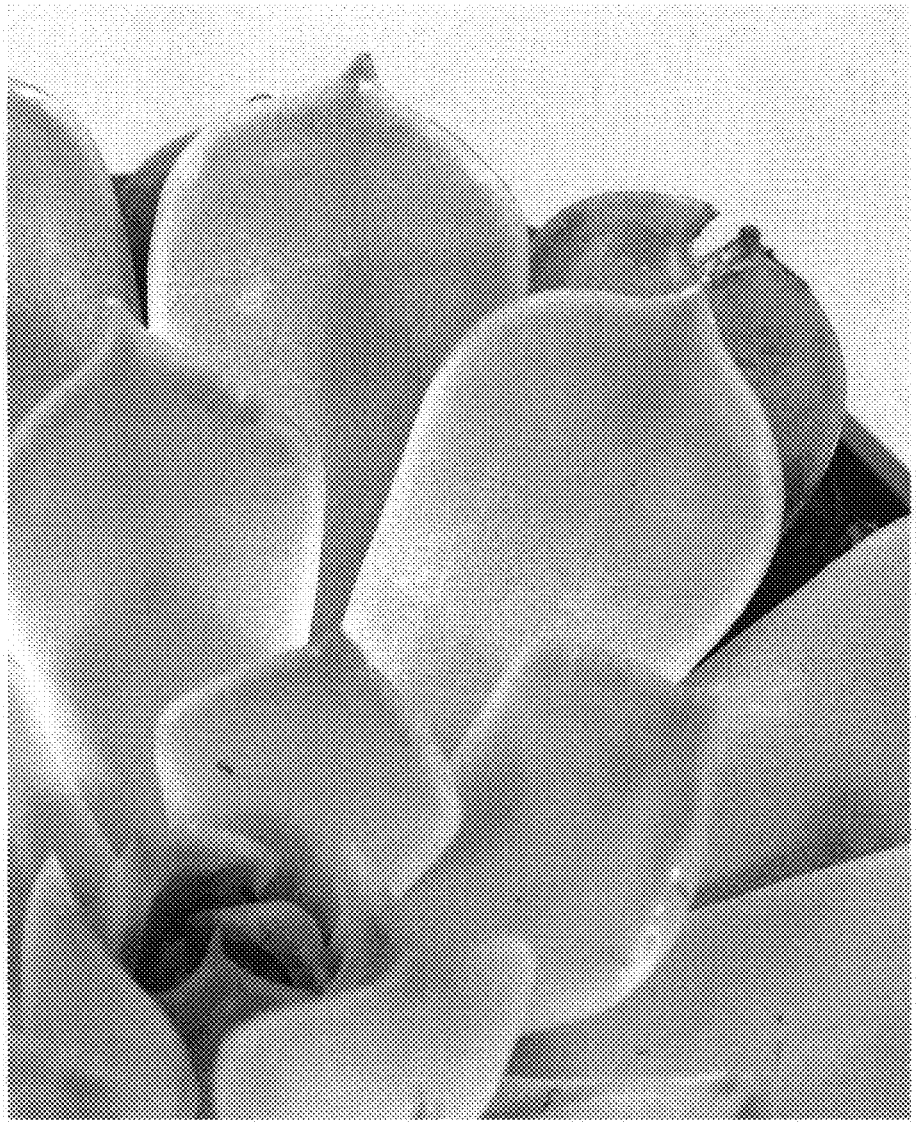
FIG. 3 illustrates, as nearly true as it is reasonably possible to make the same in color photographs of this type, the adaxial surface of the mature foliage 'TSAECH1709'.
Figure 4:
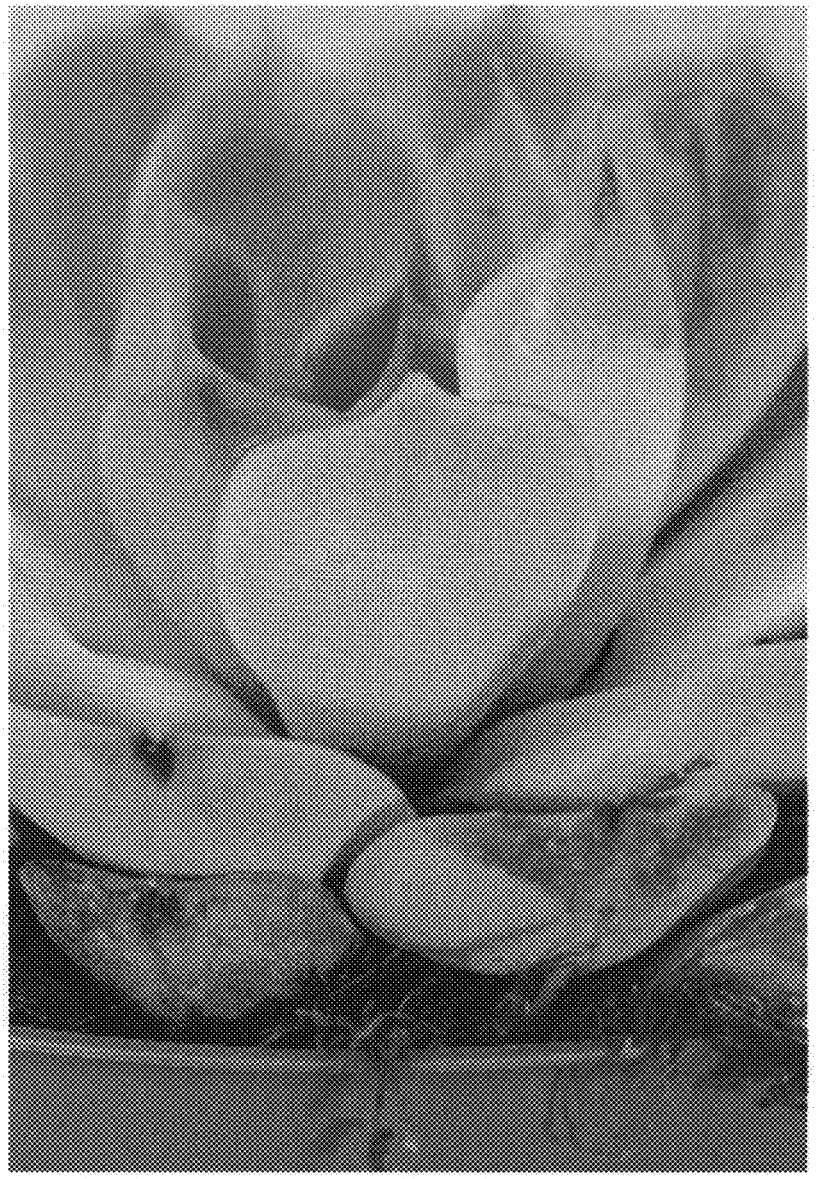
FIG. 4 illustrates, as nearly true as it is reasonably possible to make the same in color photographs of this type, the abaxial surface of the mature foliage 'TSAECH1709'.

The following observations and measurements made in February of 2018 describe averages from a sample set of six specimens of 6 months old 'TSAECH1709' plants grown in 10 cm nursery containers at commercial greenhouse in Heerhugowaard, the Netherlands. Plants were produced using conventional greenhouse production protocols for *Echeveria* plants which consisted of minimal irrigation and fertilizer applications, and chemical pest and disease control measures against mealy bug and Botrytis as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'TSAECH1709' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'TSAECH1709' and comparisons with the parent plants and closest known comparator are provided below.

Plant description:

*Growth habit*.—Succulent perennial with foliage growing in a non-branched basal rosette.

*Plant shape*.—Flattened globular.

*Height from soil level to top of foliar plane*.—4.8 cm.

*Plant spread*.—Average of 10.7 cm.

*Growth rate*.—Moderate.

*Plant vigor*.—Moderate.

*Propagation*.—Type — Leaf cuttings. Time to initiate rooting — Approximately 21 days at 18 degrees Celsius. Crop time — Approximately 35 weeks to produce a marketable plant in a 10 cm container.

*Disease and pest resistance or susceptibility*.—Neither resistance nor susceptibility to typical *Echeveria* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—Leaves in a non-branching basal rosettes; no main branches or lateral branches present.

Foliage:

*Arrangement*.—Rosette.

*Division*.—Simple.

*Attachment*.—Sessile.

*Quantity*.—Approximately 34 leaves per rosette.

*Shape*.—Thick, succulent leaves which are spatulate to obovate.

*Dimensions*.—4.7 cm long, 2.3 cm wide, and 0.5 cm thick, on average.

*Aspect*.—Slightly concave and slightly curved upward.

*Attitude*.—Younger foliage near the center of the rosette is held upright; foliage becoming progressively more relaxed towards the outer whorl of the rosette; average angle of 40 degrees from horizontal.

*Apex*.—Apiculate.

*Base*.—Cuneate.

*Margin*.—Entire; not undulated or lobed.

*Pubescence, texture and luster of the adaxial surface*.—Glabrous, smooth, and matte; moderately glaucous.

*Pubescence, texture and luster of the abaxial surface*.—Glabrous, smooth, and matte; moderately glaucous.

*Color*.—Juvenile foliage, adaxial surface — Yellow-green, nearest to RHS 148B; fading lighter towards the base, nearest to RHS 148D; narrowly margined greyed-green, nearest to RHS 192D; tipped greyed-red, nearest to a mixture of RHS 181B and 181C; the epicuticular glaucous wax covering the leaf surface is greyed-green, nearest to RHS N189D. Juvenile foliage, abaxial surface — Yellow-green, nearest to in between RHS 148B and 148C; fading to greyed-green towards the base, nearest to RHS 192A; narrowly margined greyed-green, nearest to RHS 192D; tipped greyed-red, nearest to a mixture of RHS 181B and 181C; the epicuticular glaucous wax covering the leaf surface is colored in between blue-green and greyed-green, RHS 122D and 188D. Mature foliage, adaxial surface — Nearest to in between yellow-green and greyed-green, RHS 148A and 191A; fading to greyed-green towards the base, nearest to a mixture of RHS 194C and 194D; narrowly margined green-white, nearest to RHS 196C; tipped greyed-red, nearest to RHS 182B; the epicuticular glaucous wax covering the leaf surface is greyed-green, nearest to RHS N189D. Mature foliage, abaxial surface — Yellow-green, nearest to in between RHS 147B and 148B; fading to greyed-green towards the base, nearest to a mixture of RHS 195C and 195D; narrowly margined green-white, nearest to RHS 196C; tipped greyed-red, nearest to RHS 182B; the epicuticular glaucous wax covering the leaf surface is colored in between blue-green and greyed-green, RHS 122D and 188D.

*Venation*.—No venation is visible.

*Petiole*.—No petiole; leaves are sessile.

Inflorescence: No flowering has been observed to date.

COMPARISONS WITH THE PARENT PLANT AND CLOSEST KNOWN COMPARATOR

Plants of the new cultivar 'TSAECH1709' differ from the seed parent, an unnamed *Echeveria pulidonis* x *Echeveria* hybrid 'Perle von Nurnberg' hybrid plant (not patented), in the following characteristics described in Table 1 below.

TABLE 1

| Characteristic | 'TSAECH1709' | *Echeveria pelucida* seed parent. |
|---|---|---|
| Foliage attitude. | More upright. | More relaxed. |
| General coloration of the foliage. | Greyed-green and margined pink. | Green and margined darker pink. |

Plants of the new cultivar 'TSAECH1709' differ from the pollen parent, an unnamed *Echeveria lilacina* plant (not patented), in the following characteristics described in Table 2 below.

TABLE 2

| Characteristic | 'TSAECH1709' | *Echeveria lilacina* seed parent. |
|---|---|---|
| Abundance of foliage. | More abundant; more foliar whorls per plant. | Less abundant; fewer foliar whorls per plant. |
| Foliage width. | Narrower than the seed parent. | Broader than 'TSAECH1709'. |
| General coloration of the foliage. | Greyed-green and margined pink, | Very light grey, almost white, with lilac hues. |

COMPARISONS WITH THE CLOSEST KNOWN COMPARATOR

Plants of the new cultivar 'TSAECH1709' differ from the closest known commercial comparator, *Echeveria runyonii* 'Pink Edge' (not patented), in the following characteristics described in Table 3 below.

TABLE 3

| Characteristic | 'TSAECH1709' | 'Pink Edge' |
|---|---|---|
| Foliage length. | Longer than 'Pink Edge'. | Shorter than 'TSAECH1709'. |
| General coloration of the foliage. | Greyed-green, appearing closer to green. | Greyed-green, appearing closer to blue. |
| Foliage luster. | Less glossy. | More glossy. |

That which is claimed is:

1. A new and distinct variety of *Echeveria* hybrid plant named 'TSAECH1709', substantially as described and illustrated herein.

* * * * *